US012109433B2

(12) United States Patent
Genet et al.

(10) Patent No.: US 12,109,433 B2
(45) Date of Patent: Oct. 8, 2024

(54) EFFICIENT TREATMENT OF CRANIO SPINAL CANCERS

(71) Applicant: Elekta, Inc., Atlanta, GA (US)

(72) Inventors: Louis Arunus Genet, Newcastle (AU); Stuart Julian Swerdloff, Dunedin (NZ)

(73) Assignee: Elekta, Inc., Atlanta, GA (US)

( * ) Notice: Subject to any disclaimer, the term of this patent is extended or adjusted under 35 U.S.C. 154(b) by 0 days.

(21) Appl. No.: 18/046,035

(22) Filed: Oct. 12, 2022

(65) Prior Publication Data

US 2024/0123256 A1 Apr. 18, 2024

(51) Int. Cl.
*A61N 5/10* (2006.01)

(52) U.S. Cl.
CPC ......... *A61N 5/1043* (2013.01); *A61N 5/1039* (2013.01); *A61N 5/1078* (2013.01); *A61N 2005/1087* (2013.01); *A61N 2005/1095* (2013.01)

(58) Field of Classification Search
CPC .............. A61N 2005/1096; A61N 2005/1097
See application file for complete search history.

(56) References Cited

U.S. PATENT DOCUMENTS

| 2010/0288945 | A1* | 11/2010 | Gnutzmann | G21K 1/10 |
| | | | | 250/503.1 |
| 2015/0272682 | A1* | 10/2015 | Sheng | A61B 90/17 |
| | | | | 128/845 |
| 2016/0256709 | A1* | 9/2016 | Robar | G16H 50/30 |
| 2020/0269068 | A1* | 8/2020 | Abel | A61N 5/1045 |

OTHER PUBLICATIONS

Roddy, David, et al., "HEDGEHOG: a ridge filter design for FLASH proton therapy", Canadian Association of Physicists Congress, (Jun. 7, 2022), 1 pg.

* cited by examiner

*Primary Examiner* — Eliza W Osenbaugh-Stewart
(74) *Attorney, Agent, or Firm* — Schwegman Lundberg & Woessner, P.A.

(57) ABSTRACT

Systems and techniques may be used for radiotherapy. An example system may include a fixation device arranged to receive and immobilize a patient. The example system may include a first filter arranged to extend along a first portion (e.g., a spine or cranium) of the patient, the first filter attached to the fixation device at a first location, the first filter including a plurality of beam attenuating elements. The example system may include a fixed beam proton delivery system arranged to deliver a therapeutic proton radiation dose attenuated via the first filter to the first portion of the patient.

16 Claims, 14 Drawing Sheets

EFFICIENT TREATMENT OF CRANIO SPINAL CANCERS

BACKGROUND

Radiation therapy or "radiotherapy" may be used to treat cancers or other ailments in mammalian (e.g., human and animal) tissue. One such radiotherapy technique is referred to as "gamma knife," by which a patient is irradiated using a number of lower-intensity gamma rays that converge with higher intensity and high precision at a targeted region (e.g., a tumor). In another example, radiotherapy is provided using a linear accelerator ("linac"), whereby a targeted region is irradiated by high-energy particles (e.g., electrons, high-energy photons, and the like). In another example, radiotherapy is provided using a heavy charged particle accelerator (e.g., protons, carbon ions, and the like). The placement and dose of the radiation beam is accurately controlled to provide a prescribed dose of radiation to the targeted region. The radiation beam is also generally controlled to reduce or minimize damage to surrounding healthy tissue, such as may be referred to as "organ(s) at risk" (OARs). Radiation may be referred to as "prescribed" because generally a physician orders a predefined dose of radiation to be delivered to a targeted region such as a tumor.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various embodiments discussed in the present document.

DETAILED DESCRIPTION

Figure 1A:
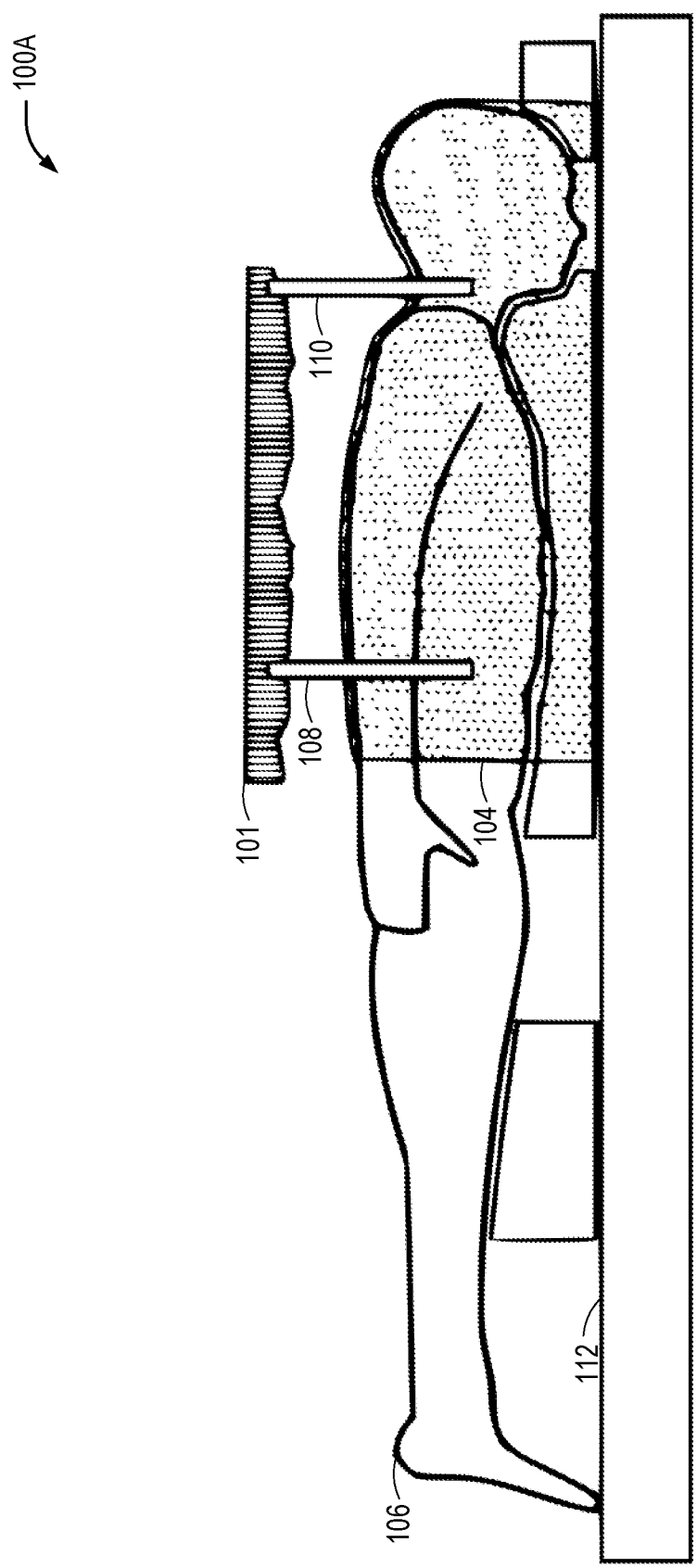
FIGS. 1A-1C illustrate views of a spinal filter device for use in radiotherapy.

In the following detailed description, reference is made to the accompanying drawings which form a part hereof, and which is shown by way of illustration-specific embodiments in which the present invention may be practiced. These embodiments, which are also referred to herein as "examples," are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not be taken in a limiting sense, and the scope of the present invention is defined by the appended claims and their equivalents.

Systems and techniques described herein may be used to for radiotherapy. For example, a particle delivery system may be arranged to deliver a therapeutic particle radiation dose. The dose may be attenuated via a filter and delivered to a first portion of a patient (e.g., a cranium, a spine optionally including a neck area, or the like). The filter may be arranged to extend along the first portion of the patient. The filter may be attached to a fixation device, which is arranged to receive or immobilize the patient. The filter may include a plurality of beam attenuating elements. In some examples, the filter may be a Homogeneous Energy Distribution GEnerator for tHerapeutic prOton beam shapinG (Hedgehog) filter.

The systems and techniques described herein provide a filter that filter is attached to a fixation device, which is also used to immobilize a patient rather than a filter being attached to a radiotherapy device. This allows for the filter to move with the patient. By moving with the patient, the patient may be immobilized less precisely. Calibration of the filter may be faster using the systems and techniques described herein. The filter may be used to spread out a Bragg peak delivered via a particle therapy delivery device or system. Spreading out the Bragg peak may lower the chances of a secondary cancer developing in the patient. This is particularly a concern in pediatric cancer patients, who may develop secondary cancers during a longer post-treatment lifespan than adult patients.

Treatment of Cranio Spinal cancers with Radiation Therapy is highly effective, but it is time consuming and technically challenging due to the length of the treatment field (typically between 36 and 50 centimeters), requiring multiple treatment fields to be delivered at different isocenters/table positions, and the non-rigid relationship between the head and the spine. Children have a higher relative frequency of Cranio Spinal cancers than adults (in part at least due to the majority of Adult cancers being Prostate and Breast, which are relatively rare in children). A treatment session may take approximately one hour, which is considerably longer than a typical treatment time slot of fifteen minutes, and many children must be anaesthetized to keep them immobile.

The use of proton therapy for pediatric cancers of the nervous system has been proven to be superior to conventional or photon therapy due to the decreased dose outside of the tumor. Excess Dose to the child's brain results in notable decrease of cognitive function, and excess dose to tissues other than tumor increase the likelihood of secondary cancers. Secondary cancers, which may occur as much as twenty years after treatment is a significant concern for children because they are much more likely to live longer post-treatment than adults. Seniors or adults tend to have mortality before a secondary cancer can form or be the cause of mortality.

An example Cranio Spinal treatment using Proton therapy involves the use of a pair of fields (Left Posterior Oblique and Right Posterior Oblique) to the brain (Cranium) both pointing to the same treatment isocenter (e.g., at the same table position), and three (or more) abutting fields each at their own isocenter (and optionally table position). In some examples, Intensity Modulated Particle Therapy (IMPT) is used, for example with Pencil Beam Scanning (e.g., Spot Scanning). A ramp up/ramp down of intensity at the junction of the fields along the axis (e.g., longitudinal) of the patient may be used. The ramp up and ramp down may be used so that mispositioning results in only a modest underdoes or overdose spread over the distance of the ramps. An example ramp length is 5 cm (e.g., enough to consume a significant part of the treatment field size). To ensure reasonably accurate positioning at the isocenter of a given treatment field (or set of fields sharing the same isocenter), Cone Beam CT imaging may be repeated for each isocenter. Treatments may be delivered in fractions (e.g., 20 fractions) of around 1.8 Gy per fraction (e.g., 36 Gy total).

FLASH Proton Therapy may be used in a variety of clinical uses, for example with a dose in the fraction of between 10 Gy and 30 Gy. In some examples, FLASH includes delivering an entire fraction in less than several hundred milliseconds. The "FLASH" effect is a reduction of effective dose to the normal tissue and organ at risk, while the effective dose to the tumor remains unchanged. Some FLASH uses a Proton energy that fully penetrates the body. However, this fails to take advantage of the zero exit dose, and the systems and techniques described herein provide a Proton energy that does not fully penetrate (e.g., does not leave) the body.

A specific approach to FLASH, called Conformal FLASH may be used, including a combination of Ion Range Compensation and spot specific range modulation. A filter may be used, such as a device colloquially referred to as a "Hedge-Hog Filter" (so named due to the shape of the device, with spine like protrusions made of the same material as an Ion range compensator, nominally Lucite or similar plastic such as ABS) with a single energy layer of IMPT. The HedgeHog filter is used to spread out a Bragg peak so that the dose is not as concentrated in a particular part of the patient.

FLASH therapy delivers a proton dose to a target quickly. In Conformal FLASH, the dose is controlled such that the Bragg peak is within the target and that there is no exit energy (or substantially diminished exit energy).

Custom, field specific, Ion Range Compensation may require time consuming manual removal and replacement of the device for each field. Overall this burden is reduced dramatically by the severe hypo-fractionation of Conformal FLASH, however it still imposes the burden for each fraction if multiple fields are involved in a single session. The present systems and techniques overcome the variety of technical issues in complexity, time of delivery of a single radiotherapy session, and overall time to deliver the course of therapy. An imaging modality capable of acquiring an entire volume to be treated in a single scan may be used (e.g., Helical CT, Spectral Helical CT, MR (MRgPT), or a CBCT system capable of automatically acquiring and concatenating multiple CBCT in to one volumetric image).

Figure 1B:
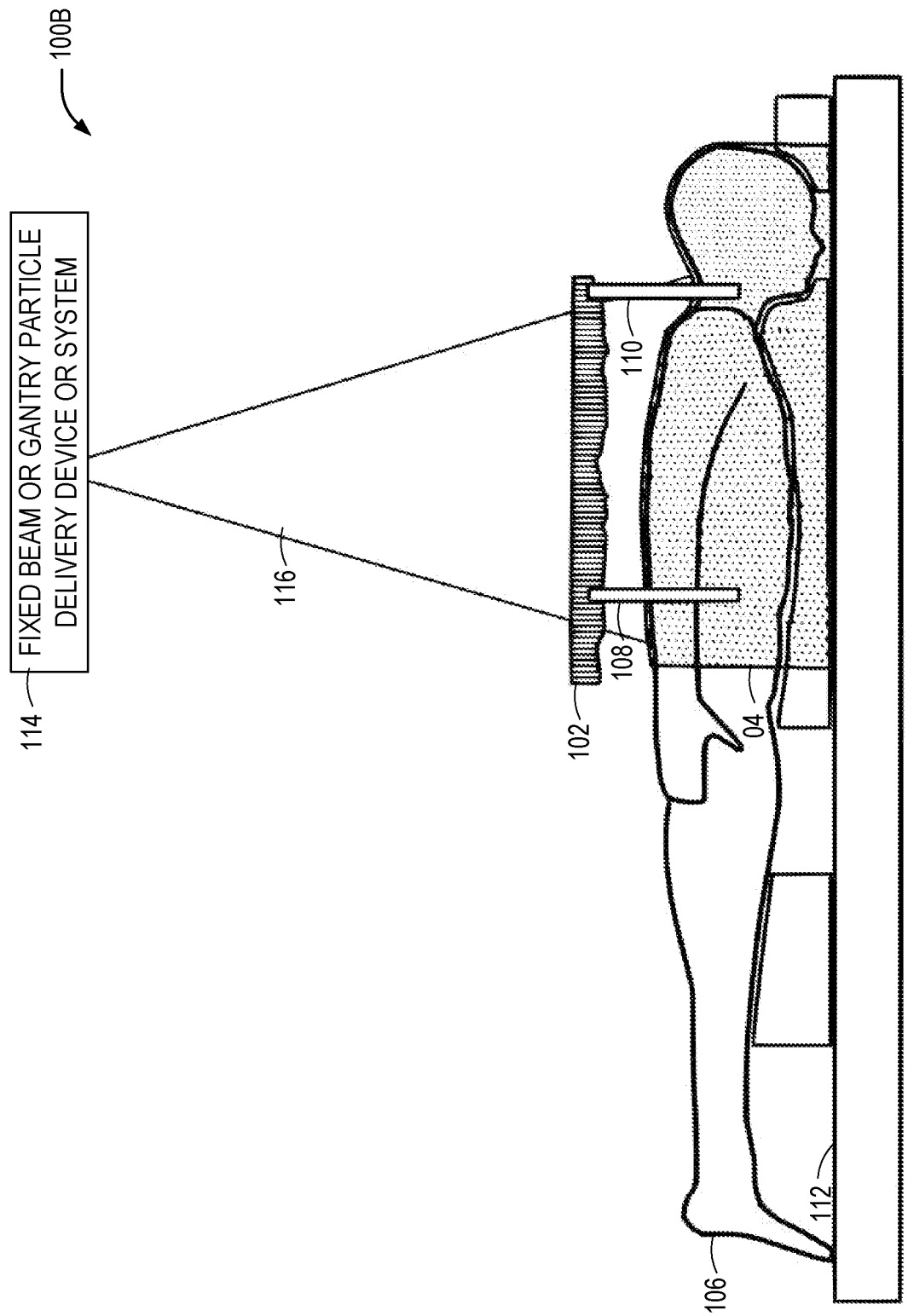
Figure 1C:
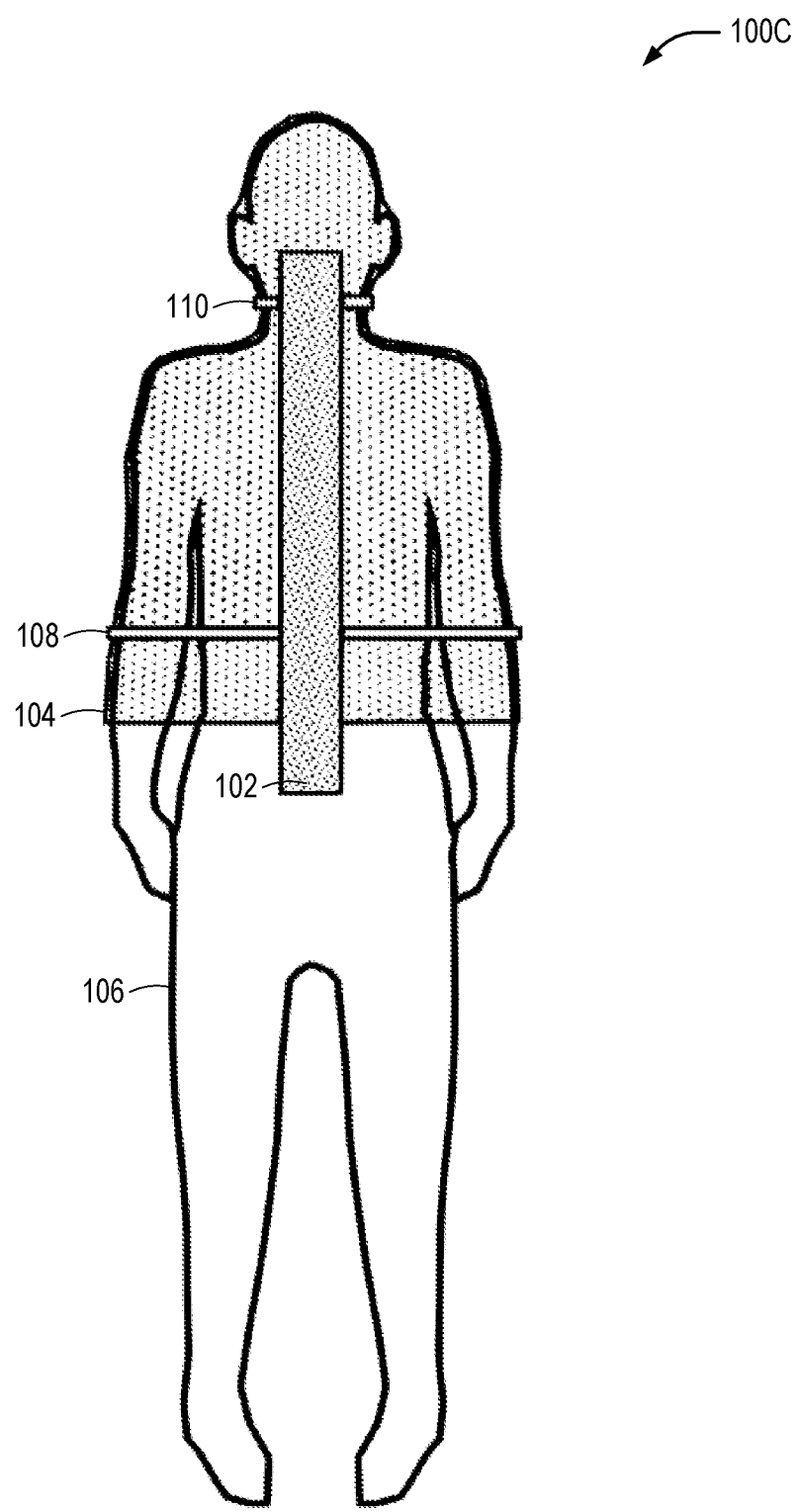

FIGS. 1A-1C illustrate views of a spinal filter device for use in radiotherapy. An example spinal filter device includes a portion of a hedgehog filter.

FIG. 1A illustrates a lateral view 100A of a patient 106 in a cast 104 (e.g., a thermoplastic cast) on a table 112. Other or additional immobilization equipment may be used in some examples. A patient specific hedgehog filter 102 is attached directly to the cast 104 at a calculated distance and position, for example via support structures 108 and 110.

FIG. 1B shows a wider lateral view 1100B showing a fixed beam proton delivery device or system 114 configured to deliver a beam 116 that is attenuated by the filter 102 before reaching the patient 106.

FIG. 1C shows a posterior view 100C, including the patient specific hedgehog filter 102 and further details of the support structures 108 and 110. The patient specific hedgehog filter 102 is shown in FIGS. 1A-1C as being affixed to the cast 104, but in other examples, the patient specific hedgehog filter 102 may be affixed to the table 112 (e.g., with the cast 104 also affixed to the table 112), to another support device, to the patient 106, or the like.

The patient specific hedgehog filter 102 extends the full range of the spine (and optionally the neck) of the patient 106. The patient specific hedgehog filter 102 may be attached to a fixation device to which the patient is also attached in some examples, such as with indexed or continuous adjustment available in the longitudinal direction of the patient specific hedgehog filter 102 relative to the patient 106.

The setup shown in FIGS. 1A-1C allow for a patient-centric orientation for filtering, rather than a radiotherapy delivery device-centric orientation. This allows for a patient coordinate system with registration of the radiotherapy deliver device. The filter 102 moves with the patient 106, which eliminates the need for precise immobilization of the patient 106. The radiotherapy process may be quicker using this setup because the radiotherapy device location may be known or recalibrated more quickly than when a filter is coupled to the radiotherapy device.

The patient-specific hedgehog filter 102 may be used with a single energy proton delivery device, to shift the delivered Bragg peak. The filter 102 may shape the field, including an ion range compensator to shape the bottom of the Bragg peak, with conical needles to shape the top of the Bragg peak (e.g., spreading out the Bragg peak). The filter 102 shifts single energy to deliver to a specific depth at different locations of the patient 106, or to have the Bragg peak spread out to different locations of the patient 106. For example, the width or spread of the Bragg peak may be controlled using the patient-specific filter 102 (e.g., including a ridge filter).

Figure 2:
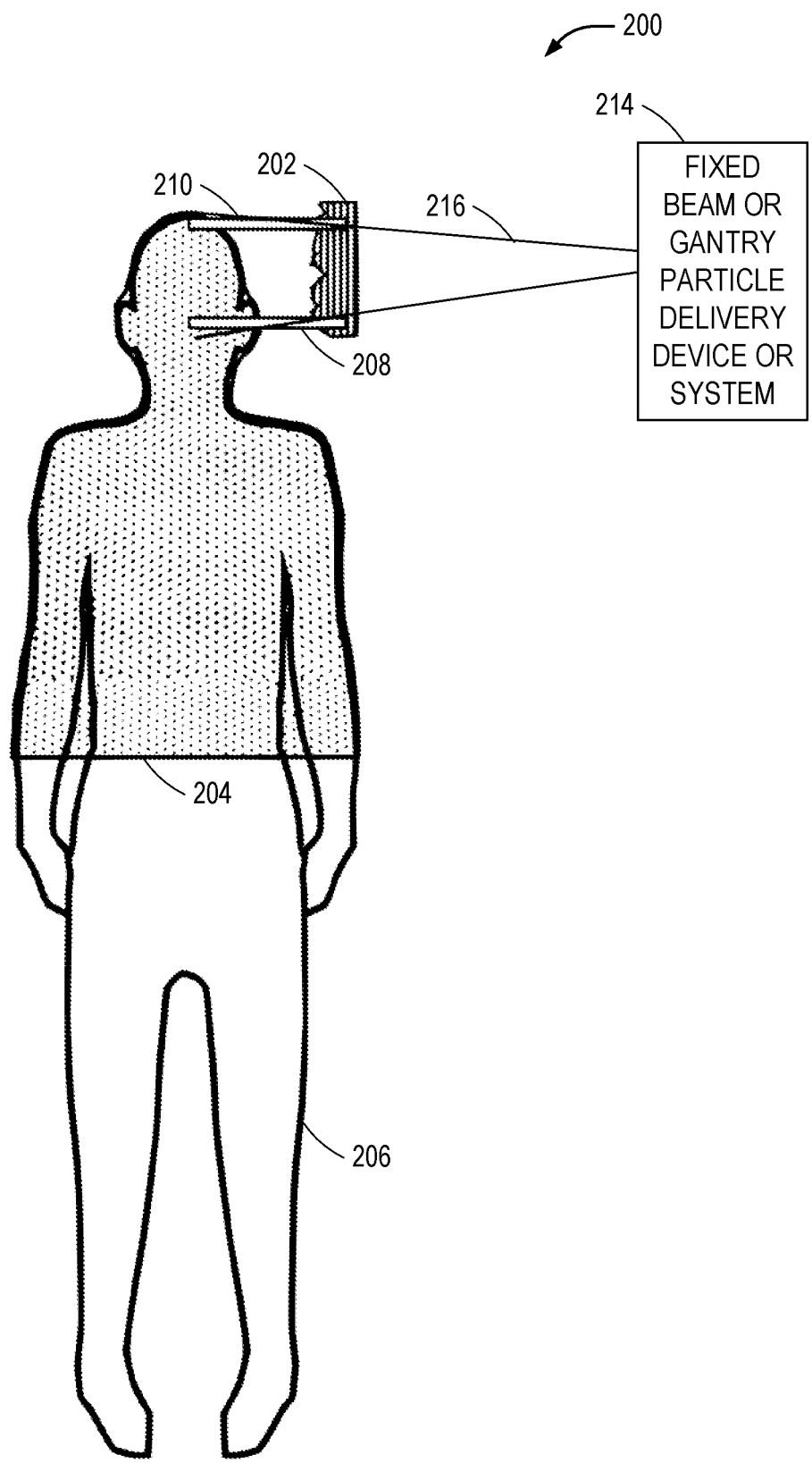
FIGS. 2-3 illustrate posterior views of a cranial filter device for use in radiotherapy.
Figure 3:
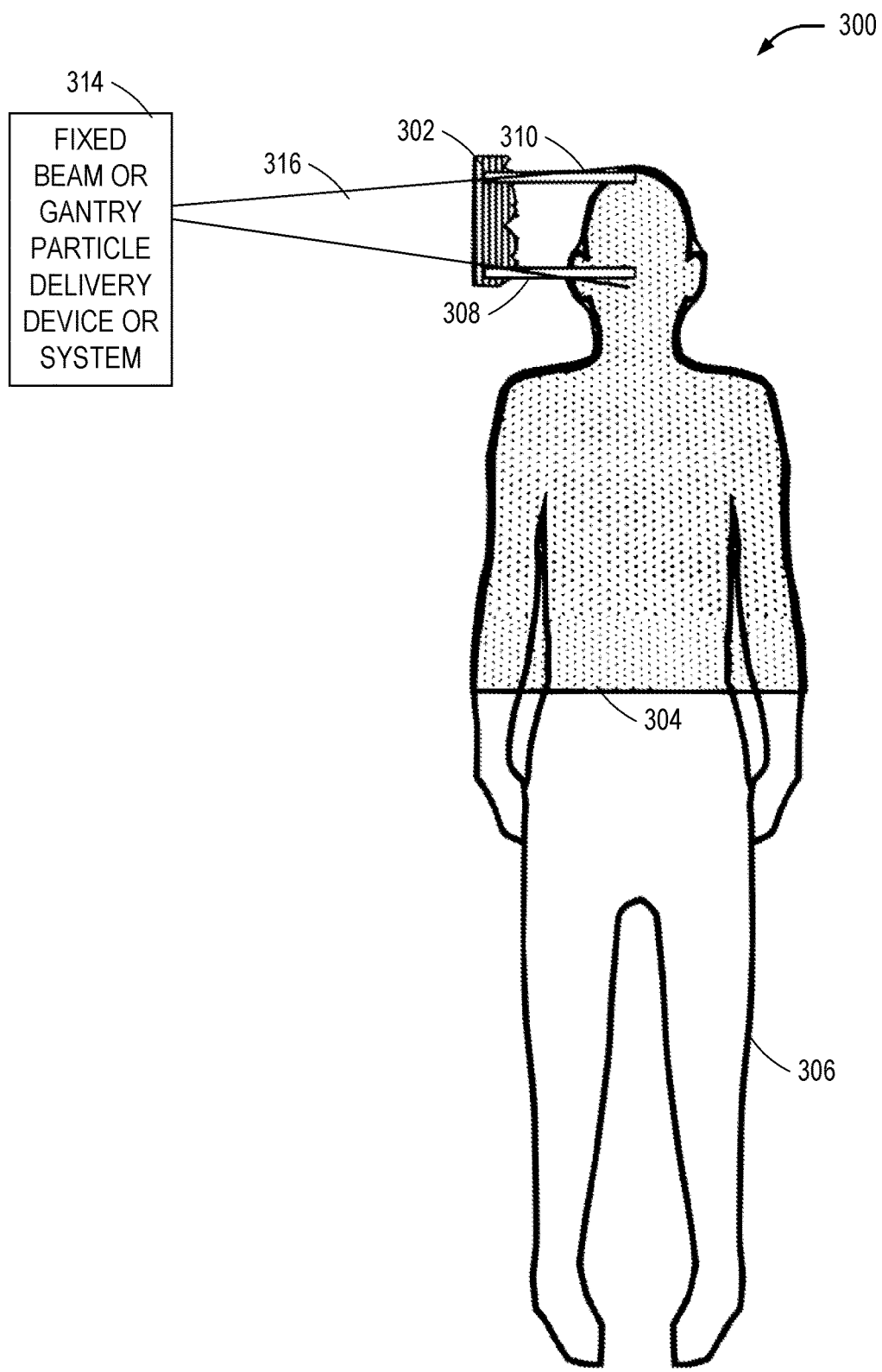

FIGS. 2-3 illustrate posterior views of a cranial filter device for use in radiotherapy. FIG. 2 shows a posterior view 200 with a lateral hedgehog filter 202. The lateral hedgehog filter 202 may be used to attenuate a lateral field 216 delivered by a fixed beam proton delivery device or system 214, to a patient 206. Similar to FIGS. 1A-1C, the lateral hedgehog filter 202 may be attached to a cast 204, a table, the patient 206, or a fixation device. In the example shown in FIG. 2, the lateral hedgehog filter 202 is affixed to the cast 204 via supports 208 and 210. The lateral hedgehog filter 202 may be positioned in a right posterior oblique position to attenuate a field from the fixed beam proton delivery device or system 214 to a cranium of the patient 206.

FIG. 3 shows a posterior view 300 with a contralateral hedgehog filter 302. The contralateral hedgehog filter 302 may be used to attenuate a contralateral field 316 delivered by a fixed beam proton delivery device or system 314, to a patient 306. Similar to FIGS. 1A-1C, the contralateral hedgehog filter 302 may be attached to a cast 304, a table, the patient 306, or a fixation device. In the example shown in FIG. 3, the lateral hedgehog filter 302 is affixed to the cast 304 via supports 308 and 310. The contralateral hedgehog filter 302 may be positioned in a left posterior oblique position to attenuate a field from the fixed beam proton delivery device or system 314 to a cranium of the patient 306.

In some examples, patients 106, 206, or 306 may be the same patient. The casts 104, 204, or 304 may be the same cast (e.g., when the patients are the same patient). The filters 202 and 302 may be the same filter, repositioned on the patient (e.g., when patients 206 and 306 are the same patient).

Figure 4:
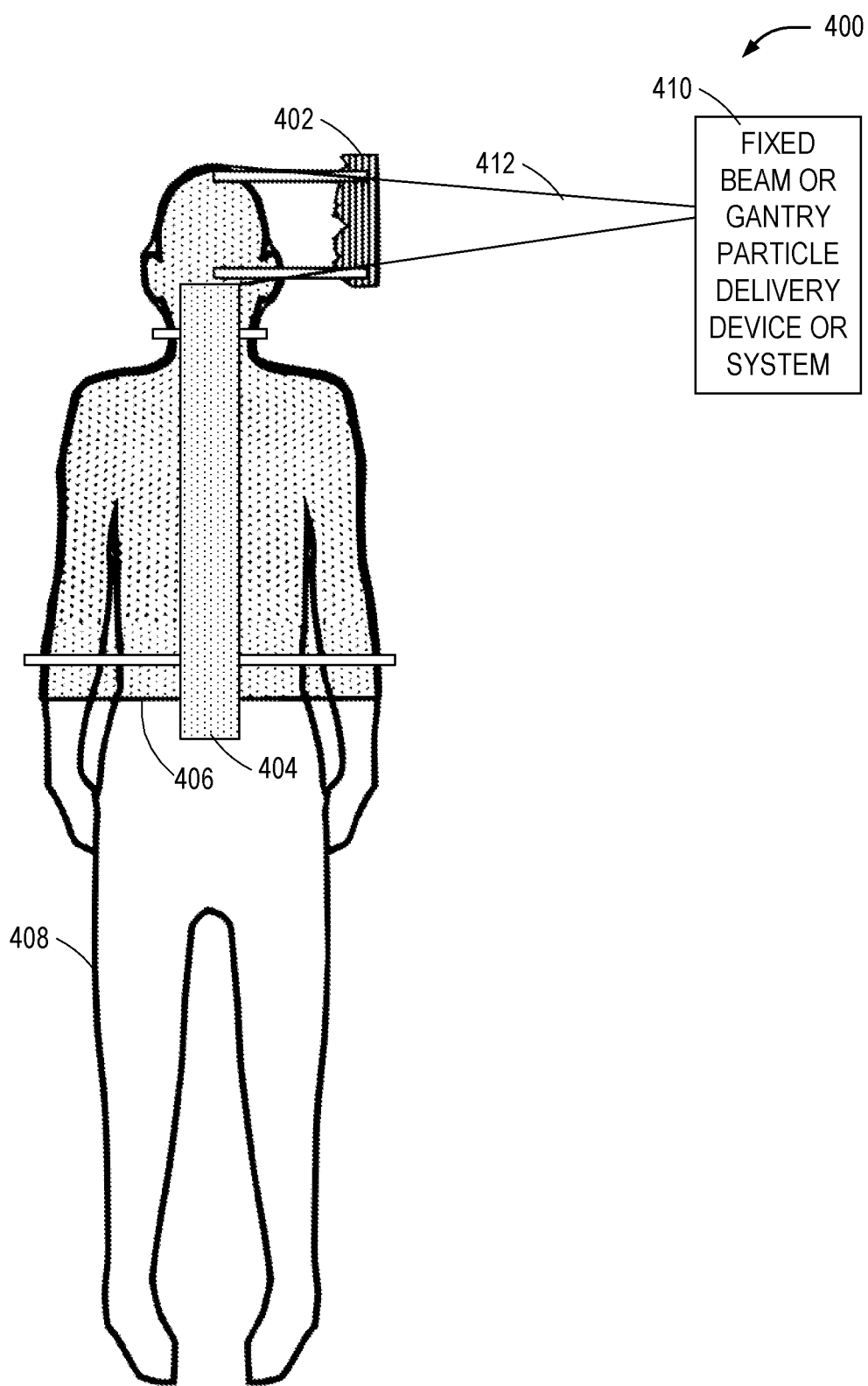
FIG. 4 illustrates a view of a cranial filter device and a spinal filter device for use in radiotherapy.

FIG. 4 illustrates a posterior view 400 of a lateral filter device 402 and a posterior filter device 404 for use in radiotherapy. Posterior view 400 shows two filters in place, although a field 412 is delivered and attenuated only via one filter at a time (e.g., filter 402 in FIG. 4). A fixed beam proton delivery device or system 410 may be used to deliver the field 412 to a cranium of a patient 408 via the lateral filter device 402, while the posterior filter device 404 is also in place. The fixed beam proton delivery device or system 410 may be moved relative to the patient 408 to deliver a field to a spine of the patient 408, attenuated by the posterior filter device 404.

In the example shown in FIG. 4, the lateral filter device 402 and the posterior filter device 404 are both attached to a fixation device 406 (e.g., a cast to immobilize the patient 408). In other examples, the lateral filter device 402 and the posterior filter device 404 may be attached to different fixation devices, but overall remain attached to a single rigid body. For example, the patient 408, the lateral filter device 402, and the posterior filter device 404 may all be stabilized to not move via a table, a fixation device, multiple fixation devices, etc. In some examples, the fixed beam proton delivery device or system 410 may output the field 412 as a long and narrow field of delivery.

In an example, an image registration system (not shown) may be used with the fixed beam proton delivery device or system 410 and the lateral filter device 402 or the posterior filter device 404. The image registration system may be used to generate a volumetric image (e.g., of the patient and a co-located filter 402 or 404). The volumetric image may be used to register the patient's treatment position with an original reference image (e.g., from a treatment plan). The image registration system may separately register the position of the lateral filter device 402 or the posterior filter device 404 with the patient 408 as specified in the treatment plan for example. The image registration system may register previous treatment session images to a current treatment session image to avoid or reduce deformations (e.g., from non-rigid motion, such as due to head or neck flexing, compression or elongation of the spine, etc.). Deformations may be avoided or reduced, which would otherwise result in dose overlap. This type of dose overlap may not be addressed by ramp up/ramp down of the abutting fields in some examples.

In some examples, three fields may be delivered (e.g., Cranial LAO, Cranial RPO, Full Spine, using one or more of the filters 402, 404, etc.), for example each in separate treatment fractions (e.g., on subsequent days). In an example, the Full Spine delivery may be given on the fixed vertical beam proton delivery device or system 410, such as with two repetitions of the 18 Gy fractions to achieve 36 Gy total. When using a full spinal length image, only one image acquisition and registration is needed for the patient position and the lateral filter device 404 positioning relative to the patient 408. In other examples, when a Proton delivery system with long field of delivery capability is not available, separate spinal fields may be defined (e.g., including ramp up/ramp down sections) with each field referencing a subset of the spinal HedgeHog filter 404.

Using one or more of the filter various setups described herein, spinal fractions no longer need to be delivered on the same beamline as the cranial fractions (required as a practical matter when multiple fields are treated on the same day without the systems and techniques described herein). Instead, a special purpose fixed vertical beamline room may be created, and a particular geometry for MR imaging (e.g., Open Bore style with the magnets on the left and right of the patient with vertical access for the Proton beam) may be provided to integrate currently existing MR technology (e.g., an open MR imaging device, such as the Upright MRI manufactured by ASG Superconductors of Genoa, Italy).

The type of MRgPT for Spinal treatment described herein, for example in combination with a general-purpose PT system, provides high throughput treatment for a pediatric center. For example, individual treatment sessions may take no more than a typical single isocenter treatment session. For a center operating 6 days per week, a child and support family may be treated and sent home in the span of one week rather than the traditionally required four weeks (e.g., based on 20 fractions, 5 fractions per week). The systems and techniques described herein therefore make it easier, quicker, and more affordable for a child to travel to a specialized, and potentially distant, pediatric center (e.g., St. Jude in the U.S., Starship in NZ, etc.).

Figure 5:
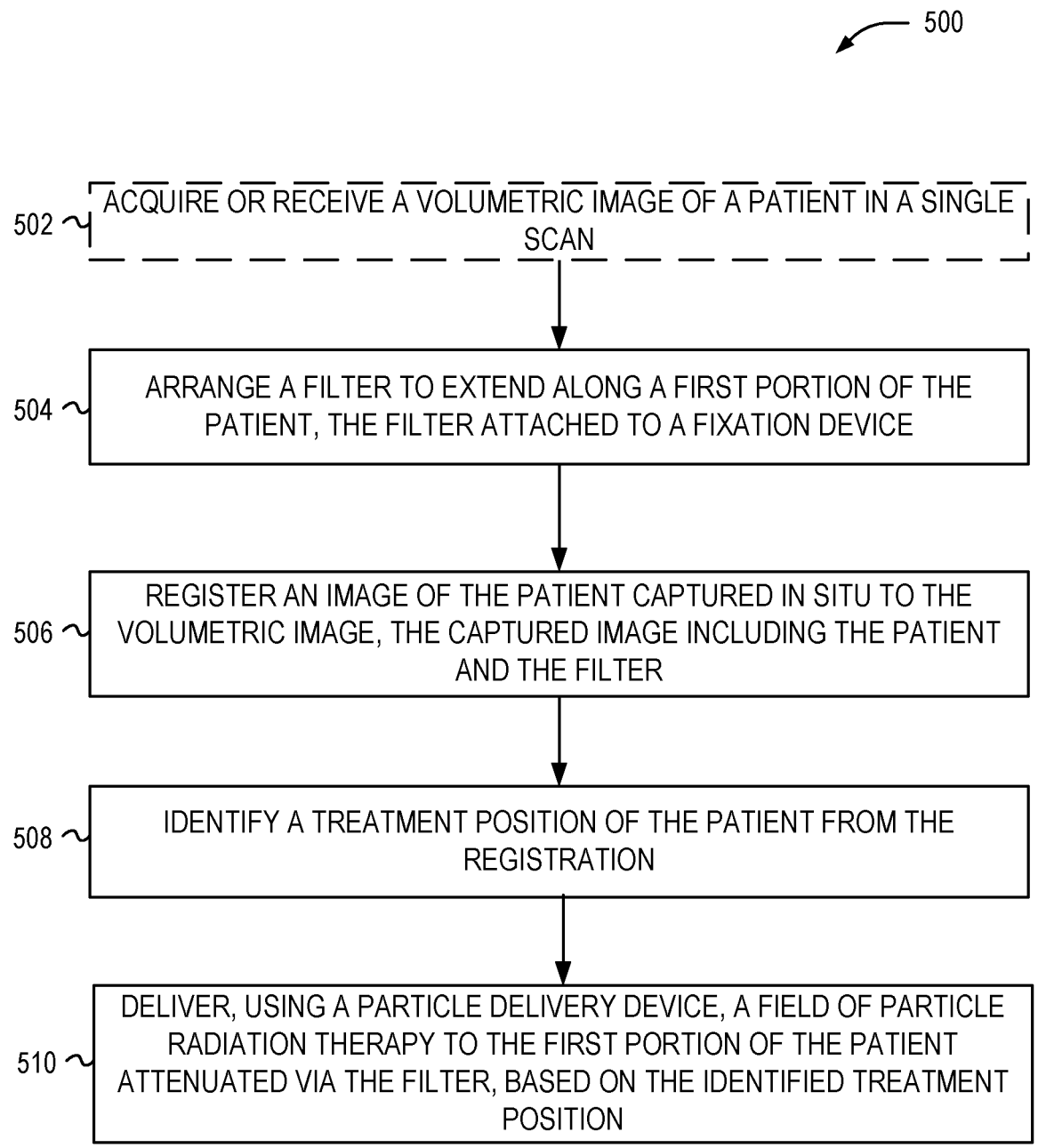
FIG. 5 illustrates a flowchart for radiotherapy treatment using a filter.

FIG. 5 illustrates a flowchart showing a technique 500 for radiotherapy treatment using a filter. The technique 500 includes an optional operation 502 to acquire a volumetric image of a patient in a single scan. The volumetric image of the patient may be captured before treatment (e.g., a day, a few days, a week, etc. before the treatment day). The volumetric image may be acquired using at least one of Helical CT, Spectral Helical CT, MR-guided Proton Therapy (MRgPT), a CBCT system configured to automatically acquire and concatenate multiple CBCT into one volumetric image, or the like.

The technique 500 includes an operation 504 to arrange a filter to extend along a spine of the patient, the filter attached to a fixation device. The filter may be a Homogeneous Energy Distribution GEnerator for tHerapeutic prOton beam shapinG (Hedgehog) filter. The fixation device may include a thermoplastic cast.

The technique 500 includes an operation 506 to register an image of the patient captured in situ to the volumetric image, the captured image including the patient and the filter. The technique 500 includes an operation 508 to identify a treatment position of the patient from the registration.

The technique 500 includes an operation 510 to deliver a field of flash proton radiation therapy to the spine of the patient using a fixed beam proton delivery device attenuated via the filter (e.g., based on the treatment position). Operation 510 may include delivering the field without anesthetizing the patient. Operation 510 may include using Ion Range Compensation. In some examples, the field of flash may include two repetitions of 18 Gy. The field of flash proton radiation therapy may be delivered using Intensity Modulated Particle Therapy (IMPT) with Pencil Beam Scanning. In some examples, a ramp up and a ramp down of intensity at a junction of fields of delivery along a longitudinal axis of the patient substantially parallel to the first filter may be used.

The technique 500 may further include delivering a second field of flash proton radiation therapy to a cranium of the patient attenuated via a second filter arranged along a posterior oblique of the patient. The second filter may be attached to the fixation device at a second location, and may be used to attenuate a therapeutic proton radiation dose delivered to a cranium of the patient via a fixed beam proton delivery device.

In some examples, the technique 500 includes registering an image captured in situ (e.g., right before, day-of radiation procedure, on table where procedure is to occur, etc.) to a volumetric image of the patient acquired in a single scan, the captured image including the patient and the first filter. In these examples, a treatment position of the patient may be identified from the registration.

The technique 500 may include delivering a first therapeutic proton radiation dose to a left posterior oblique or delivering a second therapeutic proton radiation dose to a right posterior oblique of the cranium of the patient. In examples where both the first and second dose are delivered, they may point to a same treatment isocenter in the patient.

Figure 6:
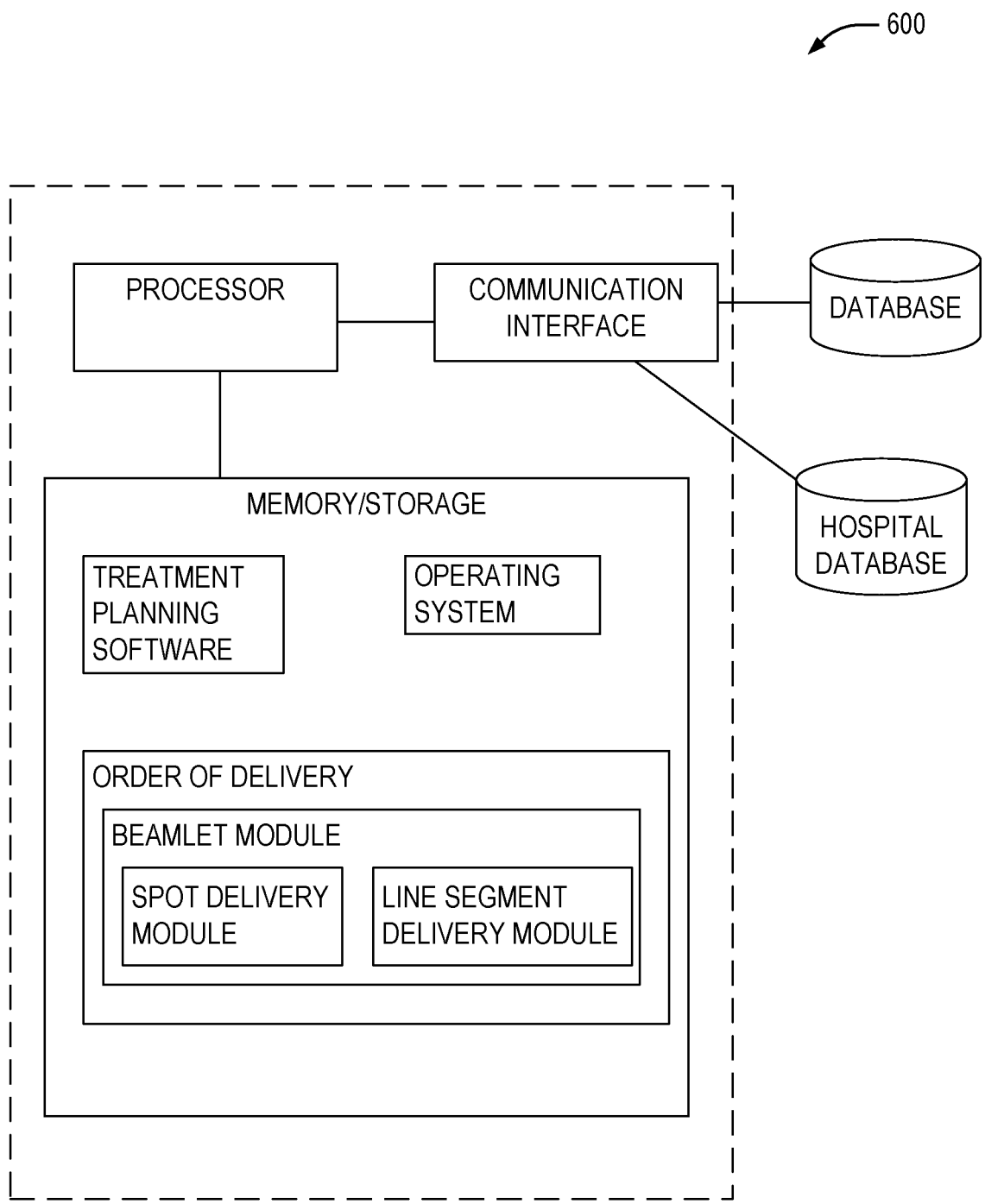
FIG. 6 illustrates generally an example of a system, such as may include a particle therapy system controller, according to an example.

FIG. 6 illustrates generally an example of a system 600, such as may include a particle therapy system controller, according to an example. The system 600 may include a database or a hospital database. The particle therapy system controller may include a processor, communication interface, or memory. The memory may include treatment planning software, an operating system, or a delivery controller. The delivery controller may include a beamlet module for determining or planning spot delivery (e.g., using a spot delivery module) or line segment delivery (e.g., using a line segment delivery module).

In an example, the spot delivery module or the beamlet module may be configured to plan size of beamlets, location of a target or spot, or the like. The beamlet module may be used to determine an order of delivery of beamlets, for example in a spiral pattern as described herein. The order of delivery module may be in communication with the treatment planning software for planning delivery of beamlets. For example, the treatment planning software may be used to determine or plan gantry angle, gantry speed, beamlet size, spiral pattern (e.g., clockwise or counterclockwise), angle range for a particular spiral pattern (e.g., every ten degrees of the gantry rotation), or the like.

The processor may implement the plan, such as by communicating, via the communication interface or otherwise, to components used to implement the plan (e.g., to control devices or components, such as those described below with reference to FIG. 8). In an example, the communication interface may be used to retrieve stored information from a database or a hospital database (e.g., patient information, past procedure information for the patient or other patients, procedure instructions, information about particular devices or components, or the like).

Figure 7:
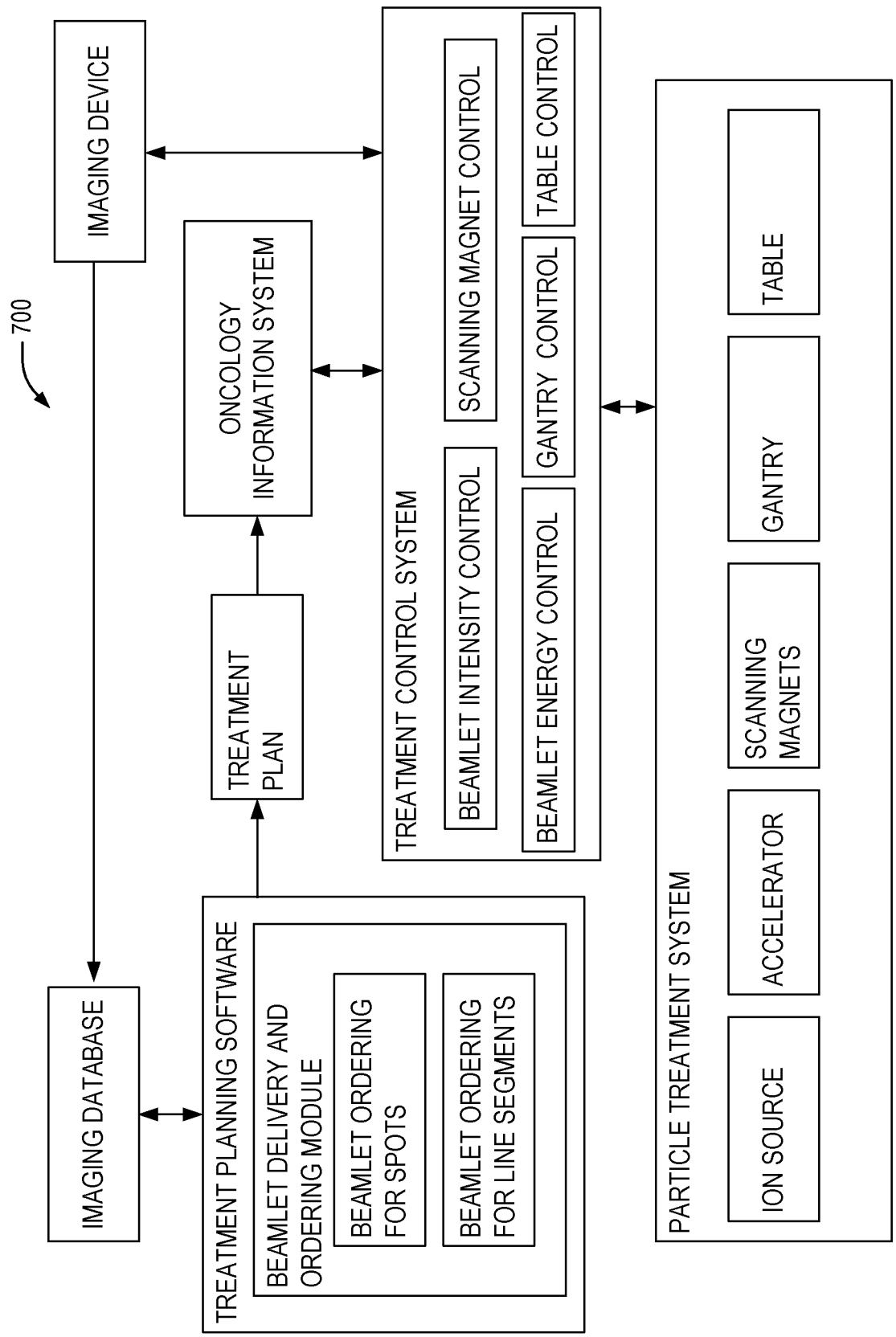
FIG. 7 illustrates generally an example of a radiation therapy system, such as may include a particle treatment system and an imaging acquisition device, according to an example.

FIG. 7 illustrates generally an example of a radiation therapy system 700, such as may include a particle treatment system and an imaging acquisition device, according to an example. The particle treatment system includes an ion source, an accelerator, and scanning magnets, each of which is described in more detail below with respect to FIG. 8. The particle treatment system includes a gantry and a table, where the gantry may be mounted on the table, affixed to the table, or stabilized with respect to the table. The table may hold a patient. The gantry may be a rotating gantry, and may rotate with respect to the table (e.g., around the table) or with respect to the patient (and the table or a portion of the table may rotate with the gantry).

The particle treatment system may communicate with a treatment control system, which may be used to control actions of the particle treatment system. The treatment control system may communicate with an imaging acquisition device (e.g., to receive images taken by the imaging acquisition device or an imaging database) or an oncology information system. The oncology information system may provide treatment plan details to the treatment control system, such as received from treatment planning system. The treatment control system may use the treatment plan to control the particle treatment system (e.g., activate the gantry, the ion source, the accelerator, the scanning magnets, a particle beam, or the like). The treatment control system, for example, may include a beamlet intensity control, a beamlet energy control, a scanning magnet control, a table control, a gantry control, etc. In an example, the beamlet intensity control and the beamlet energy control may be used to activate a beamlet of a particular size or to target a particular location. The scanning magnetic control may be used to deliver beamlets according to the treatment plan, for example in a spiral pattern. The gantry control or the table control may be used to rotate the gantry.

The treatment planning software may include components such as a beamlet delivery and ordering module, with, for example, separate controls for beamlet ordering for spots or line segments. The treatment planning software is described in more detail above with respect to FIG. 6. The treatment planning software may access an imaging database to retrieve images or store information. When a treatment plan is completed, the treatment planning software may send the plan to an oncology information system for communication with the treatment control system.

Figure 8:
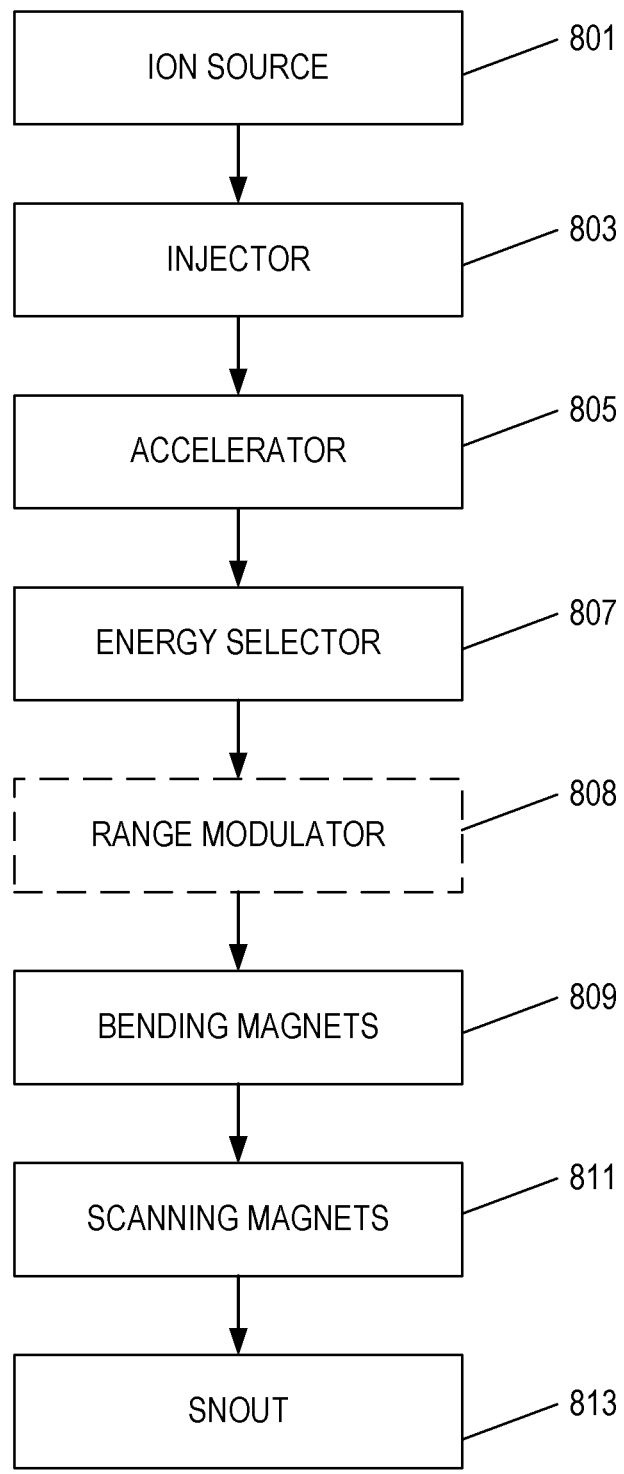
FIG. 8 illustrates generally a particle treatment system that may include a radiation therapy output configured to provide a proton therapy beam, according to an example.

FIG. 8 illustrates an example of a particle treatment system 800 that may include a radiation therapy output configured to provide a proton therapy beam. The particle treatment system 800 includes an ion source 801, an injector 803, an accelerator 805, an energy selector 807, a plurality of bending magnets 809, a plurality of scanning magnets 811, and a snout 813.

The ion source 801, such as a synchrotron (not shown) may be configured to provide a stream of particles, such as protons. The stream of particles is transported to an injector 803 that provides the charged particles with an initial acceleration using a Coulomb force. The particles are further accelerated by the accelerator 805 to about 10% of the speed of light. The acceleration provides energy to the particles, which determines the depth within tissue the particles may travel. The energy selector 807 (e.g., a range scatter) may be used to select the energies of the protons to be delivered to the patient. In an example called passive scattering, an optional range modulator 808 (e.g., also called a ridge filter or a range modulation wheel) may be utilized to broaden the beam to fit the tumor. After selecting energies, a set of bending magnets 809 may be utilized to transport the stream of protons into a radiation therapy treatment room of a hospital. Further, scanning magnets 811 (e.g., x-y magnets) are used to spread the proton beam to, or trace, an exact image of the tumor shape. A snout 813 is used to further shape the proton beam. In some examples, the stream of particles may be composed of carbon ions, pions, or positively charged ions.

Figure 9:
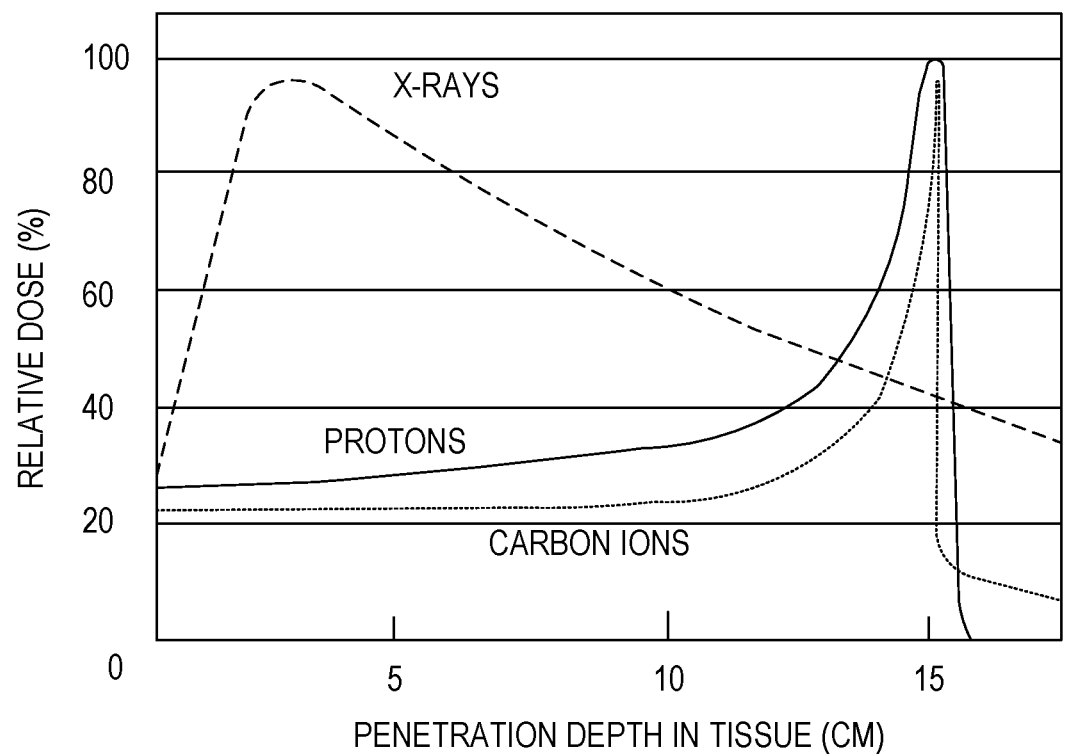
FIG. 9 illustrates generally radiation dose depths in human tissue for various types of particles, according to an example.

FIG. 9 provides an illustration of a comparison of radiation dose depths for various types of particles in human tissue. As shown, the relative depth of penetration into human tissue of photons (e.g., x-rays) versus protons versus carbon ions is provided (e.g., including any radiation dose provided at a distance beneath the surface, including secondary radiation or scatter). Each radiation dose is shown relative to the peak dose for a proton beam having a single energy which has been set to 100%.

The mono-energetic (e.g., single energy) proton beam indicates a plateau region starting at approximately 25% that gradually increases until approximately 10 cm depth in tissue where it rapidly increases to the Bragg Peak at 15 cm and then advantageously falls to zero within a short distance. No additional dose is delivered to the end of the Bragg peak.

The photon beam (e.g., labelled as X-rays) indicates the initial build up due to electron scatter (e.g., the primary means by which X-rays deliver dose to tissue is through transfer of energy to electrons in the tissue). This is followed by an exponential fall off, which continues past the distal edge of the target, which is at approximately 15 cm depth in the diagram. The x-ray beam has an entrance (skin) dose set to match that of the proton beam. With normalization (e.g., scaling) at 15 cm depth, the dose due to x-rays is at 40% of the dose provided by proton beam, while the x-ray beam has a peak dose of greater than 95% ("near" 100%) at approximately 3 cm depth. If the x-ray data is renormalized to achieve 100% dose at 15 cm, the peak dose at approximately 3 cm depth would be approximately 240%, in a location where dose is not desired (e.g., prior to the target). Therefore, with x-rays, a considerable amount of dose is delivered prior to the target and an appreciable amount of dose is delivered past the target.

The mono-energetic carbon beam shows a plateau region at the entrance dose that is lower than the proton beam. The carbon beam has a sharper Bragg Peak that falls more precipitously than the proton beam, but the carbon beam has a tail (e.g., known as a "spallation tail", where some of the Carbon nuclei shatter into Helium ions) that has approximately 10% additional dose, or less, past the desired target by several centimeters. The carbon ion beam has an undesired entrance and skin dose compared to the proton beam, but the carbon ion beam has a non-trivial dose delivered past the target.

Figure 10:
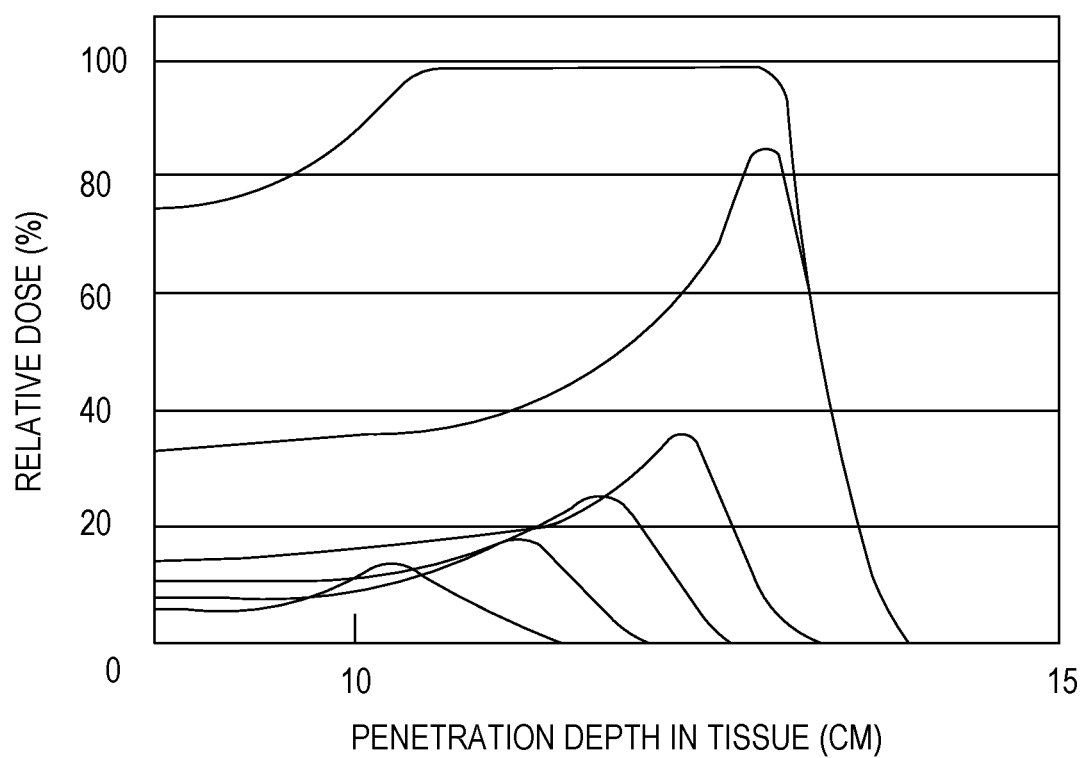
FIG. 10 illustrates generally a spread-out Bragg Peak, according to an example.

FIG. 10 provides an illustration of a spread-out Bragg peak (SOBP). The SOBP, displays a relative depth dose curve for the combination of a set of proton beams of various initial energies each of which has had some spread in energy (e.g., variable absorption of energy in tissue). The desired result of having a uniform dose for a target of a particular thickness. As shown, the target is shown with a proximal depth of approximately 10 cm, a distal depth of approximately 13 cm, and a target thickness of approximately 3 cm. Within the target, the dose is quite uniform (with an average normalized at 100%). The diagram does not start at 0 cm depth and is not explicitly showing the entrance (skin) dose, but the nature of the entrance region of proton beams is a relatively flat depth dose curve. Typically, the entrance (skin) dose will be approximately 70% of the target dose (e.g., shown at the far right edge of the x-axis). A SOBP may be obtained using a variety of approaches, including using a scattered proton beam with modulation of the energy (variable absorption) utilizing a variety of devices (e.g., a static ridge filter or a dynamic range modulation wheel), or by selection of a number of mono-energetic proton beams that do not undergo scatter.

Figure 11:
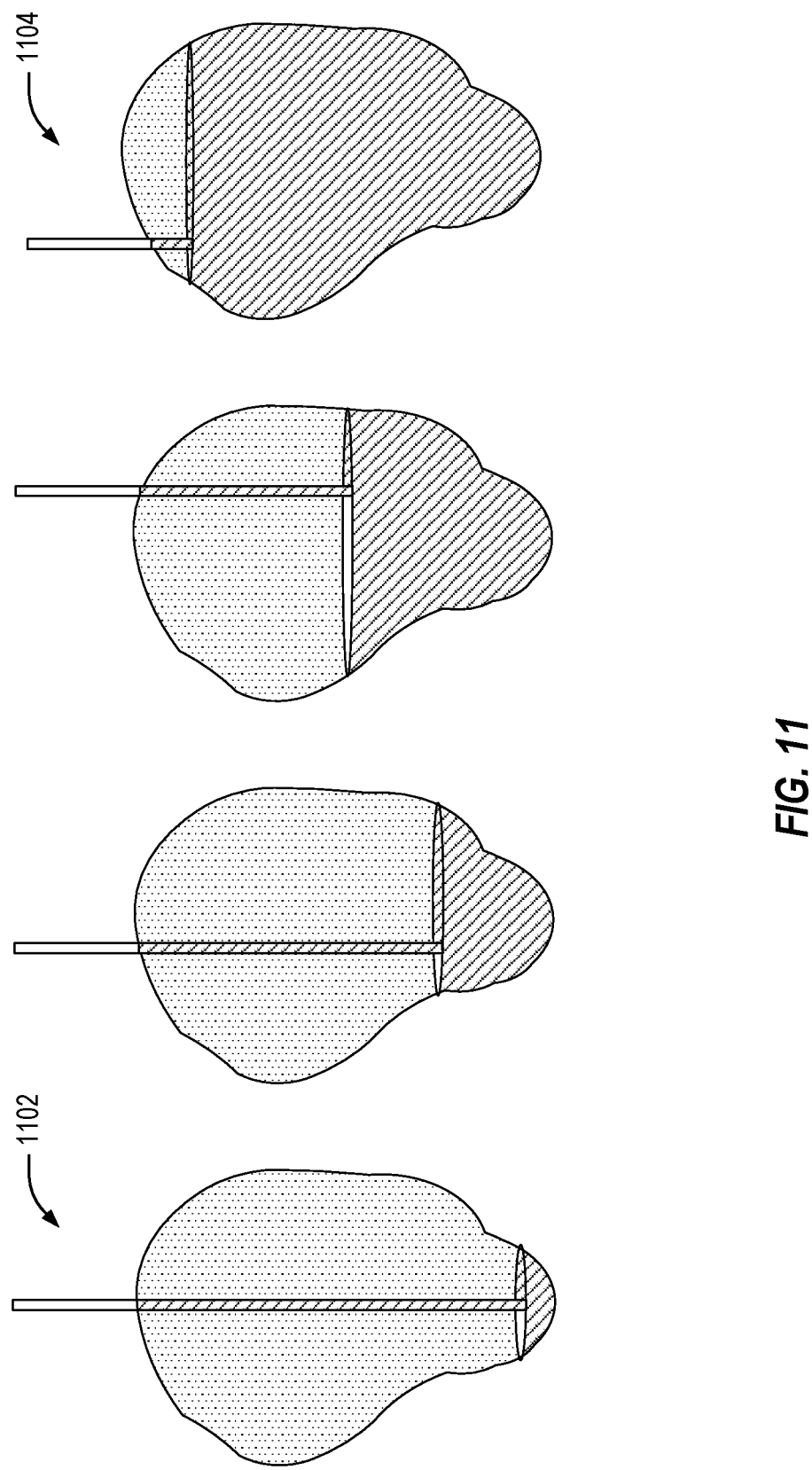
FIG. 11 illustrates generally pencil beam scanning of an irregular shape volume from distal edge to proximal edge, according to an example.

FIG. 11 provides an illustration of a Pencil Beam Scanning of an irregular shape volume from a distal edge (e.g., bottom) to a proximal (e.g., top) edge. As shown, the irregular shaped tumor volume is irradiated layers of protons. For example, a first time snapshot 1102 shows a first layer of protons being delivered, and a later time snapshot 1104 shows that most of the layers have been delivered. Each layer has its own cross-sectional area to which the protons having the same energy are delivered. The total radiation dose is provided as a layer-by-layer set of beamlets. Each layer of may have different energies. The most common means of specifying and delivering the set of beamlets to the cross-sectional area is to define and deliver beamlets having a constant diameter ("spot size") to a selection of grid points on each layer. While the majority of the dose from the beamlet is delivered to the targeted layer, a significant amount of dose is delivered along the path to the targeted layer. The dose to proximal layers from beamlets defined for distal layers is accounted for in the specification of the beamlets defined for the proximal layers. The ability to individually specify the number of particles (e.g., the meterset) for a given beamlet ensures that each part of the volume being irradiate receives the desired dose.

Figure 12:
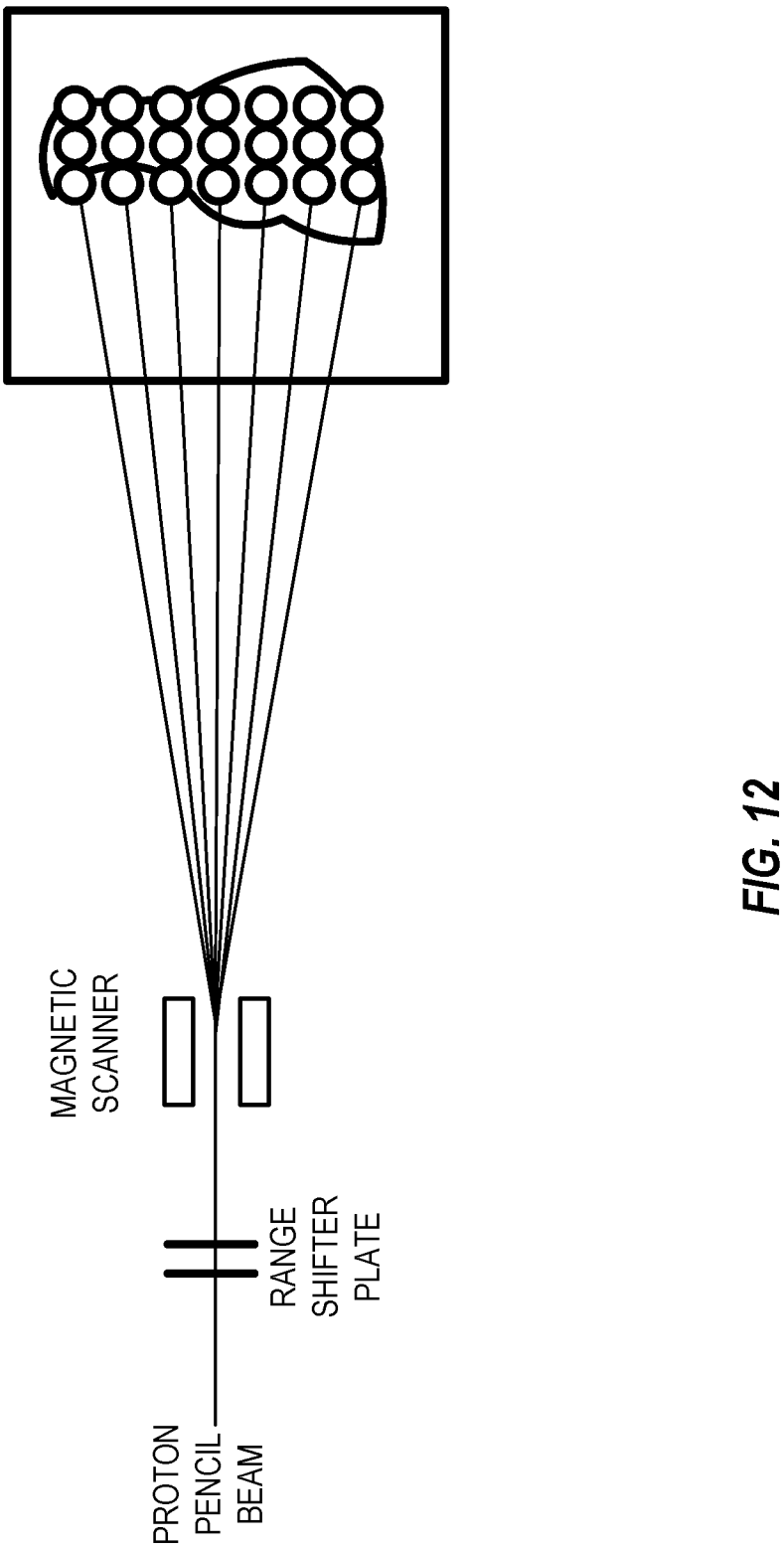
FIG. 12 illustrates generally a diagram of an active scanning proton beam delivery system, according to an example.

FIG. 12 provides an illustration of a diagrammatic representation of a typical active scanning proton beam delivery system. As shown, a single layer of a pencil beam scan is being delivered, with a grid of spots depicted on a patient in conjunction with a contour of the cross-sectional area to which particles are to be delivered. An incoming monoenergetic proton beamlet has a specified amount of its energy absorbed by the Range Shifter (e.g., in FIG. 12 it is a Range Shifter plate), resulting in a beamlet with the desired energy to achieve a certain depth for the Bragg Peak in the patient to treat the specified layer. A magnetic scanner, which has the ability to deflect the particles in both a vertical and a horizontal direction. The strength of the magnetic fields may be adjusted to control the deflection in the direction perpendicular to the magnetic field and the incoming beamlet. The rate at which the magnetic field strengths may be adjusted determines the rate at which the scanning may take place. For example, the intensity of the proton beamlet in combination with the scanning rate determines how much dose may be delivered to a specific area (e.g., in FIG. 12, a "spot") in a particular amount of time (e.g., particles/unit area). In theory, the magnetic field strengths may be adjusted independently of each other (in a fashion similar to the children's toy "Etch a Sketch®", provided by Spin Master™, Toronto, Canada; with the pencil beamlet intensity being a variable not available in the children's toy). The most common scheme for scanning is to scan in one direction quickly and to scan in the perpendicular direction more slowly in a raster fashion, similar to how early televisions were controlled (e.g., Cathode Ray Tube (CRT), which use electrons instead of protons), but arbitrary patterns may be scanned (similar to the previously mentioned toy). Delivery of distinct spots is achieved by incrementing the scanning magnetic field strength and throttling the pencil beam intensity between increments.

The above detailed description includes references to the accompanying drawings, which form a part of the detailed description. The drawings show, by way of illustration but not by way of limitation, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a," "an," "the," and "said" are used when introducing elements of aspects of the invention or in the embodiments thereof, as is common in patent documents, to include one or more than one or more of the elements, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "comprising," "including," and "having" are intended to be open-ended to mean that there may be additional elements other than the listed elements, such that after such a term (e.g., comprising, including, having) in a claim are still deemed to fall within the scope of that claim. Moreover, in the following claims, the terms "first," "second," and "third," etc., are used merely as labels, and are not intended to impose numerical requirements on their objects.

The present invention also relates to a computing system adapted, configured, or operated for performing the operations herein. This system may be specially constructed for the required purposes, or it may comprise a general-purpose computer selectively activated or reconfigured by a computer program (e.g., instructions, code, etc.) stored in the computer. The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

In view of the above, it will be seen that the several objects of the invention are achieved and other advantageous results attained. Having described aspects of the invention in detail, it will be apparent that modifications and variations are possible without departing from the scope of aspects of the invention as defined in the appended claims. As various changes could be made in the above constructions, products, and methods without departing from the scope of aspects of the invention, it is intended that all matter contained in the above description and shown in the accompanying drawings shall be interpreted as illustrative and not in a limiting sense.

The above description is intended to be illustrative, and not restrictive. For example, the above-described examples (or one or more aspects thereof) may be used in combination with each other. In addition, many modifications may be made to adapt a particular situation or material to the teachings of the invention without departing from its scope. While the dimensions, types of materials and example parameters, functions, and implementations described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

Example 1 is a system for radiotherapy comprising: a fixation device arranged to receive and immobilize a patient; a first filter arranged to extend along a first portion of the patient, the first filter attached to the fixation device, the first filter including a plurality of beam attenuating elements; and a particle delivery system arranged to deliver a therapeutic particle radiation dose attenuated via the first filter to the first portion of the patient.

In Example 2, the subject matter of Example 1 includes, wherein the particle delivery system comprises one or more fixed beams or a gantry.

In Example 3, the subject matter of Examples 1-2 includes, wherein the first filter is a Homogeneous Energy Distribution GEnerator for tHerapeutic prOton beam shapinG (Hedgehog) filter.

In Example 4, the subject matter of Examples 1-3 includes, wherein the first filter is attached to the fixation device at a first location, and wherein the system further comprises a second filter arranged along a posterior oblique of the patient, the second filter attached to the fixation device at a second location, and wherein the particle delivery system is further arranged to deliver a therapeutic proton radiation dose attenuated via the second filter to a second portion of the patient.

In Example 5, the subject matter of Example 4 includes, wherein the first portion of the patient is a spine and the second portion of the patient is a cranium.

In Example 6, the subject matter of Examples 4-5 includes, wherein the particle delivery system arranged to deliver the therapeutic proton radiation dose to deliver a first therapeutic proton radiation dose to a left posterior oblique and to deliver a second therapeutic proton radiation dose to a right posterior oblique of a cranium of the patient, wherein each of the first and second dose point to a same treatment isocenter in the patient.

In Example 7, the subject matter of Examples 1-6 includes, wherein the fixation device includes a thermoplastic cast.

In Example 8, the subject matter of Examples 1-7 includes, wherein the particle delivery system arranged to deliver the therapeutic particle radiation dose without anesthetizing the patient.

In Example 9, the subject matter of Examples 1-8 includes, wherein the particle delivery system is further arranged to use Intensity Modulated Particle Therapy (IMPT) with Pencil Beam Scanning.

In Example 10, the subject matter of Example 9 includes, wherein the particle delivery system is further arranged to use a ramp up and a ramp down of intensity at a junction of fields of delivery along a longitudinal axis of the patient substantially parallel to the first filter.

In Example 11, the subject matter of Examples 1-10 includes, an image registration system to: register an image captured in situ to a volumetric image of the patient acquired in a single scan, the captured image including the patient and the first filter; and identify a treatment position of the patient from the registration.

In Example 12, the subject matter of Examples 9-11 includes, wherein the volumetric image is acquired using at least one of Helical CT, Spectral Helical CT, or MR-guided Proton Therapy (MRgPT).

In Example 13, the subject matter of Examples 1-12 includes, wherein the particle delivery system is further arranged to deliver the therapeutic particle radiation dose based on conformal FLASH using Ion Range Compensation.

In Example 14, the subject matter of Examples 1-13 includes, wherein the therapeutic particle radiation dose is delivered in a field as a proton radiation dose and wherein fractions of the field include two repetitions of 18 Gy.

Example 15 is a method comprising: receiving a volumetric image of a patient in a single scan; arranging a filter to extend along a first portion of the patient, the filter attached to a fixation device; registering an image of the patient captured in situ to the volumetric image, the captured image including the patient and the filter; identifying a treatment position of the patient from the registration; and delivering, using a particle delivery device, a field of particle radiation therapy to the first portion of the patient attenuated via the filter, based on the identified treatment position.

In Example 16, the subject matter of Example 15 includes, wherein the filter is a Homogeneous Energy Distribution GEnerator for tHerapeutic prOton beam shapinG (Hedgehog) filter.

In Example 17, the subject matter of Examples 15-16 includes, registering an image captured in situ to a volumetric image of the patient acquired in a single scan, the captured image including the patient and the first filter; and identifying a treatment position of the patient from the registration.

In Example 18, the subject matter of Example 17 includes, wherein the volumetric image is acquired using at least one of Helical CT, Spectral Helical CT, or MR-guided Proton Therapy (MRgPT).

In Example 19, the subject matter of Examples 15-18 includes, wherein the first filter is attached to the fixation device at a first location, and further comprising arranging a second filter along a posterior oblique of the patient, the second filter attached to the fixation device at a second location, and delivering, using the particle delivery device, a therapeutic proton radiation dose attenuated via the second filter to a second portion of the patient.

In Example 20, the subject matter of Example 19 includes, wherein the first portion of the patient is a spine and the second portion of the patient is a cranium.

Example 21 is at least one machine-readable medium including instructions that, when executed by processing circuitry, cause the processing circuitry to perform operations to implement of any of Examples 1-20.

Example 22 is an apparatus comprising means to implement of any of Examples 1-20.

Example 23 is a system to implement of any of Examples 1-20.

Example 24 is a method to implement of any of Examples 1-20.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:

1. A system for radiotherapy comprising:
 a fixation device arranged to receive and immobilize a patient;
 a first filter arranged to extend along a first portion of the patient, the first filter attached to the fixation device via one or more supports, the first filter including a plurality of beam attenuating elements;
 a particle treatment system, including an ion source and a plurality of magnets, the particle treatment system arranged to deliver a therapeutic particle radiation dose attenuated via the first filter to the first portion of the patient, wherein the first filter is attached to the fixation device at a first location; and
 a second filter arranged along a posterior oblique of the patient, the second filter attached to the fixation device at a second location, wherein the particle treatment system is further arranged to deliver a therapeutic proton radiation dose attenuated via the second filter to a second portion of the patient, and wherein the therapeutic proton radiation dose attenuated via the second filter is delivered to the second portion of the patient from a vertical beamline, and the therapeutic proton radiation dose attenuated via the first filter is delivered to the first portion along a different beamline than the vertical beamline.

2. The system of claim 1, wherein the particle treatment system comprises one or more fixed beams or a gantry.

3. The system of claim 1, wherein the first filter is a static ridge filter.

4. The system of claim 1, wherein the vertical beamline is delivered along a spine of the patient and wherein the different beamline is delivered along a cranium of the patient.

5. The system of claim 1, wherein the particle treatment system arranged to deliver the therapeutic particle radiation dose is to deliver a first therapeutic proton radiation dose to a left posterior oblique and to deliver a second therapeutic proton radiation dose to a right posterior oblique of a cranium of the patient, wherein each of the first and second dose point to a same treatment isocenter in the patient.

6. The system of claim 1, wherein the fixation device includes a thermoplastic cast.

7. The system of claim 1, wherein the particle treatment system is arranged to deliver the therapeutic particle radiation dose without anesthetizing the patient.

8. The system of claim 1, wherein the particle treatment system is further arranged to use Intensity Modulated Particle Therapy (IMPT) with Pencil Beam Scanning.

9. The system of claim 8, wherein the particle treatment system is further arranged to use a ramp up and a ramp down of intensity at a junction of fields of delivery along a longitudinal axis of the patient substantially parallel to the first filter.

10. The system of claim 1, wherein a volumetric image is acquired using at least one of Helical CT, Spectral Helical CT, or MR-guided Proton Therapy (MRgPT).

11. The system of claim 1, wherein the particle treatment system is further arranged to deliver the therapeutic particle radiation dose based on conformal FLASH using Ion Range Compensation.

12. The system of claim 1, wherein the therapeutic particle radiation dose is delivered in a field as a proton radiation dose and wherein fractions of the field include two repetitions of 18 Gy.

13. A method comprising:
    receiving a volumetric image of a patient in a single scan;
    arranging a first filter to extend along a first portion of the patient, the first filter attached to a fixation device via one or more supports at a first location;
    arranging a second filter along a posterior oblique of the patient, the second filter attached to the fixation device at a second location;
    registering an image of the patient captured in situ to the volumetric image, the captured image including the patient, the first filter, and the second filter;
    identifying a treatment position of the patient from a registration;
    delivering, from a particle treatment system including an ion source and a plurality of magnets, a field of particle radiation therapy to the first portion of the patient attenuated via the first filter, based on the identified treatment position; and
    delivering, using the particle treatment system, a therapeutic proton radiation dose attenuated via the second filter to a second portion of the patient from a vertical beamline, and wherein the therapeutic proton radiation dose attenuated via the first filter is delivered to the first portion along a different beamline than the vertical beamline.

14. The method of claim 13, wherein the first filter is a static ridge filter.

15. The method of claim 13, wherein the volumetric image is acquired using at least one of Helical CT, Spectral Helical CT, or MR-guided Proton Therapy (MRgPT).

16. The method of claim 13, wherein the vertical beamline is delivered along a spine of the patient and wherein the different beamline is delivered along a cranium of the patient.

* * * * *